United States Patent
Naegerl

(10) Patent No.: US 7,066,963 B2
(45) Date of Patent: Jun. 27, 2006

(54) TIBIA PLATEAU FOR A REPLACEMENT JOINT

(75) Inventor: Hans Naegerl, Gleichen (DE)

(73) Assignee: HJS Gelenk-System GmbH, Munich (DE)

( * ) Notice: Subject to any disclaimer, the term of this patent is extended or adjusted under 35 U.S.C. 154(b) by 0 days.

(21) Appl. No.: 11/065,482

(22) Filed: Feb. 25, 2005

(65) Prior Publication Data

US 2005/0197710 A1    Sep. 8, 2005

(30) Foreign Application Priority Data

Feb. 26, 2004    (DE) ............... 20 2004 003 133 U

(51) Int. Cl.
*A61F 2/38*    (2006.01)

(52) U.S. Cl. ............... 623/20.32; 623/20.29

(58) Field of Classification Search ... 623/20.16–20.32
See application file for complete search history.

(56) References Cited

U.S. PATENT DOCUMENTS

| | | | |
|---|---|---|---|
| 4,057,858 A * | 11/1977 | Helfet | ............ 623/20.11 |
| D248,771 S * | 8/1978 | Groth, Jr. | |
| 4,808,185 A | 2/1989 | Penenberg et al. | |
| 5,137,536 A | 8/1992 | Koshino | |
| 5,556,432 A * | 9/1996 | Kubein-Meesenburg et al. | ............ 623/20.21 |
| 6,120,543 A | 9/2000 | Kubein-Meesenburg et al. | |
| 6,235,060 B1 | 5/2001 | Kubein-Meesenburg et al. | |
| 2004/0002767 A1* | 1/2004 | Wyss | ............ 623/20.27 |
| 2004/0138755 A1* | 7/2004 | O'Connor et al. | ........ 623/20.32 |
| 2005/0055101 A1* | 3/2005 | Sifneos | ............ 623/20.32 |
| 2005/0209701 A1* | 9/2005 | Suguro et al. | ........... 623/20.27 |
| 2005/0209703 A1* | 9/2005 | Fell | ............ 623/20.33 |

FOREIGN PATENT DOCUMENTS

| | | |
|---|---|---|
| DE | 40 06 714 A1 | 9/1990 |
| GB | 2 120 943 A | 12/1983 |
| WO | WO 94/09724 | 5/1994 |

* cited by examiner

*Primary Examiner*—Suzette J-J Gherbi
(74) *Attorney, Agent, or Firm*—Crowell & Moring LLP

(57) ABSTRACT

A tibia plateau for a replacement joint, particularly an endoprosthesis for a human knee joint, in which the head and socket artificial joint parts have convex and concave articulation surfaces, respectively, and the articulation surfaces are arranged in pairs, so that the functional surfaces which are formed can roll against one another along a curved contact line, especially a circularly arcuate contact line, formed on each articulation surface. A gently sloping bulge (1) is formed in the area (4) adjacent the functional surfaces (2) which bulge prevents excessive rolling movement and lateral displacement of the joint parts relative to each other.

10 Claims, 3 Drawing Sheets

TIBIA PLATEAU FOR A REPLACEMENT JOINT

This invention relates to the design of the tibia plateau of a joint replacement, in particular an endoprosthesis for the human knee joint.

U.S. Pat. No. 5,556,432 (=DE 42 02 717); U.S. Pat. No. 6,120,543 (=DE 195 21 597) and U.S. Pat. No. 6,235,060 (=DE 196 46 891) relate to artificial joints, particularly an endoprosthesis for replacing a natural joint. The endoprosthesis is comprised of at least two artificial joint components having curved articulation surfaces with a curved contact line, especially an arcuate contact line, formed on each articulation surface. The articulation surfaces are arranged in relation to one another in pairs so that the contact lines can roll along one another. When the joint parts are moved relative to one another, there may be an excessively wide rolling and consequently a pivoting movement of the joint parts with respect to one another and/or there may be a lateral displacement, either of which may result in a malfunction of the joint.

SUMMARY OF THE INVENTION

It is an object of the present invention to provide an improved artificial joint.

Another object of the invention is to provide a joint implant in which pivoting movement is limited and lateral displacement is prevented.

A further object of the invention is to provide an artificial joint implant in which there is a practical safety barrier which expands the indications in which the joint may be used.

In addition to limiting the motion of the dimeric chain of articulation, the structural design should mechanically limit the functional movement but leave the original functional surfaces unchanged.

These and other objects are achieved in accordance with the present invention by providing a tibia plateau of a joint replacement endoprosthesis comprising head and socket artificial joint parts having respective convex and concave functional articulation surfaces formed thereon, the artificial joint parts being arranged in pairs in contact with each other such that the functional articulation surfaces can roll against one another along a curved contact line formed on the functional articulation surfaces, in which a sloping bulge is formed adjacent the functional surfaces, which bulge limits the rolling movement and lateral displacement of the artificial joint parts.

In accordance with a preferred aspect of the invention the joint replacement endoprosthesis is an endoprosthesis for a human knee joint.

In accordance with a further preferred aspect of the invention, the curved contact line is an arcuate line.

Additional preferred embodiments and features of the present invention are described hereinafter.

BRIEF DESCRIPTION OF THE DRAWINGS

The invention will be described in further detail hereinafter with reference to illustrative preferred embodiments of a human knee joint shown in the accompanying drawing figures, in which.

DETAILED DESCRIPTION OF PREFERRED EMBODIMENTS

Figure 1:
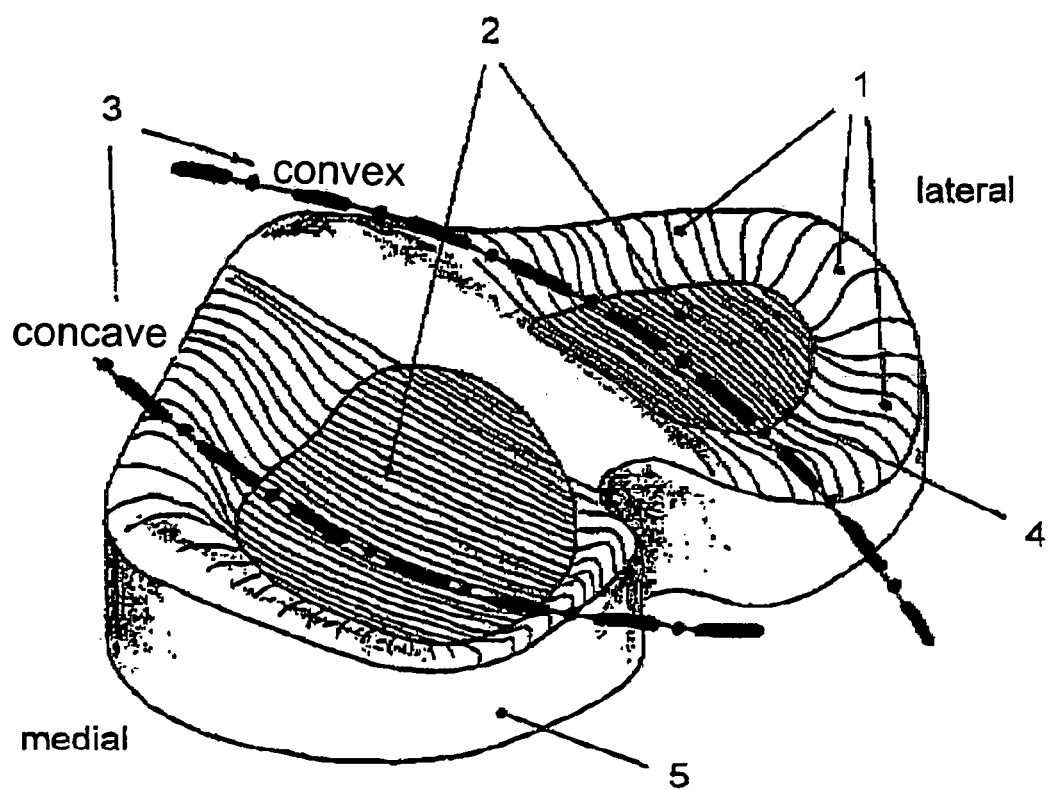
FIG. 1 is a perspective view of the tibia plateau of a knee joint replacement according to the present invention.

The tibia plateau 5 of an endoprosthesis for an illustrative example of a human knee joint comprises two functional surfaces 2, one of which on the lateral side has a convex curvature, while the other of which on the medial side has a concave curvature. In the drawings, the respective curvatures of the functional surfaces are indicated by broken lines identified by the reference numeral 3. According to the present invention, a gently sloping bead or bulge 1 is formed adjacent the edge areas 4 of the functional surfaces 2. This bulge 1 forms a mechanical limit for the second joint part, which in this case would be a femur joint replacement part 6 (See FIG. 3). When the joint moves and the femur part 6 rolls on the functional surfaces 2 of the tibia part, the femur part is prevented from rolling further than desired and/or from lateral displacement by striking against the bulge 1.

Figure 2:
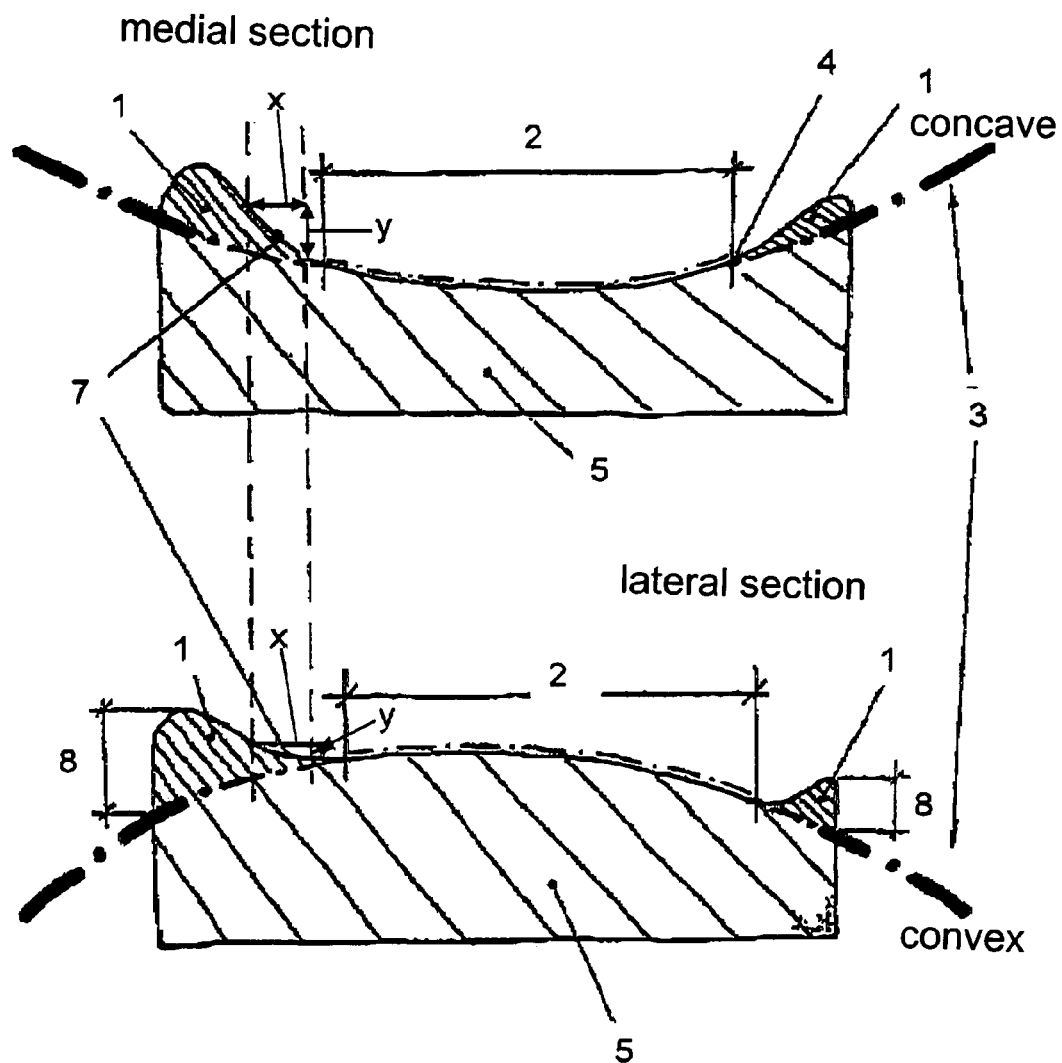
FIG. 2 is a lateral sectional diagram through the medial and lateral parts of the tibia plateau.
Figure 3:
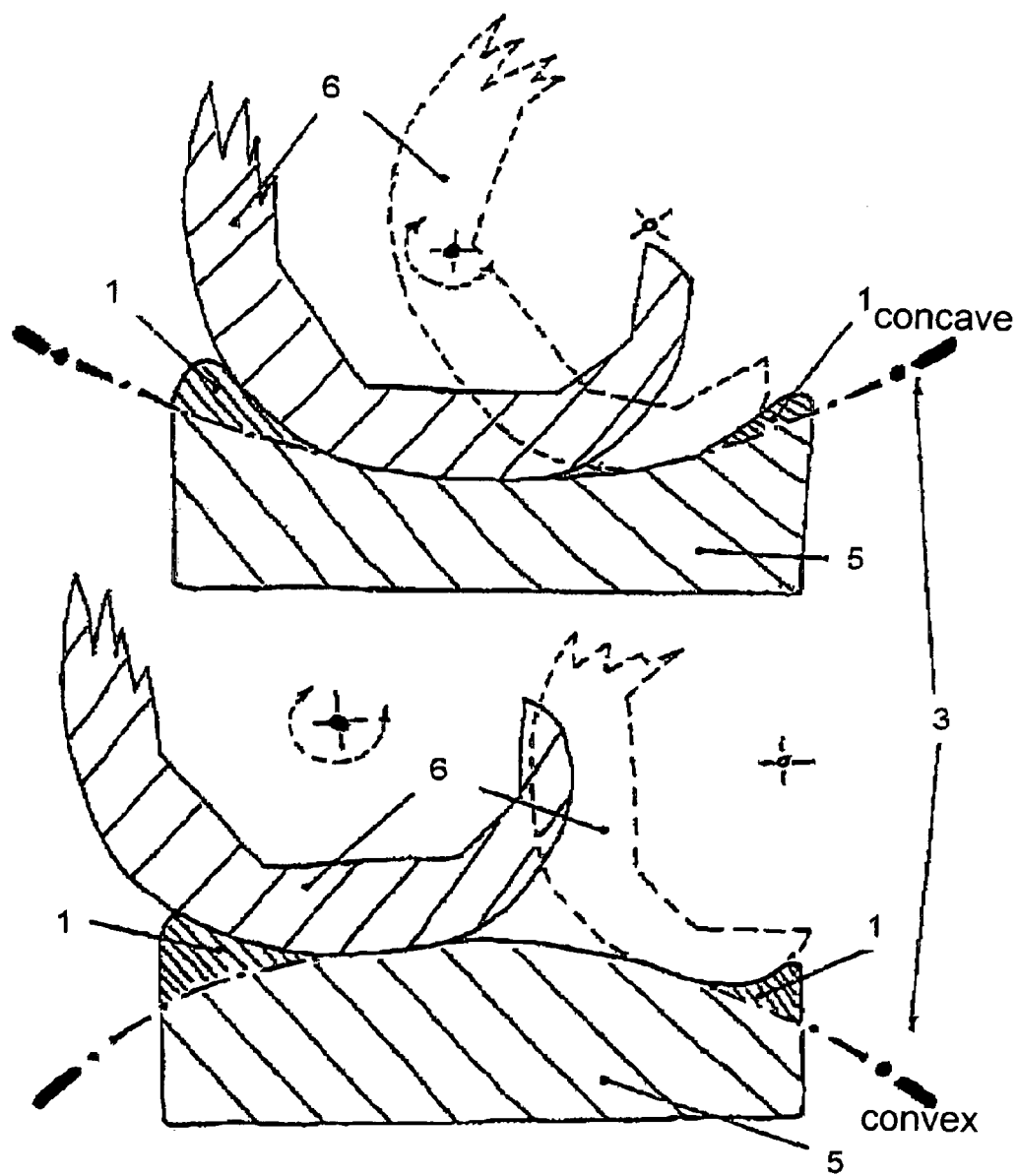
FIG. 3 is a lateral sectional diagram through the joint head and socket which illustrates how the movement is limited.

The sectional diagrams in FIGS. 2 and 3 each show both the medial section with the concave curvature and the lateral section with the convex curvature of the functional surfaces 2. The bulge 1 may be formed in all directions or only in certain directions as viewed from the functional surfaces 2, i.e., it may be designed to continuously surround the functional surfaces 2 or to be discontinuous and be formed only at discrete locations around the periphery of each functional surface. The slope 7 of the bulge 1 may be the same in all directions, or the slope may be different in different directions. The slope 7 of the bulge 1 also may be linear (y/x), or the slope may have a concave curvature (dy/dx), and it may be the same in all directions or it may be linear in some directions and concave in other directions. Similarly, the height 8 of the bulge 1 may be the same in all directions, or the bulge may have different heights in different directions as viewed from the functional surfaces.

Practical use of the bulge 1 on the tibia plateau of the endoprosthesis according to the present invention has shown that the measure of the present invention has for the first time made the artificial joint as described in the prior publications referred to in the introductory portion of this application, fully functional. The application of the inventive measure is not limited to the example of the artificial knee joint. Rather, the invention is also applicable to other types of replacement joints.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A tibia plateau for a joint replacement endoprosthesis comprising head and socket artificial joint parts having respective convex and concave functional articulation surfaces formed thereon, said artificial joint parts being arranged in pairs consisting of the head and the socket in contact with each other such that the functional articulation surfaces of the head and the socket are capable of rolling against one another along a curved contact line formed on the functional articulation surfaces, wherein a sloping bulge is formed adjacent the functional surfaces, which bulge limits the rolling movement and lateral displacement of the artificial joint parts, and wherein the bulge continuously surrounds the functional articulation surfaces in all directions as viewed from the functional articulation surfaces.

2. The tibia plateau for a joint replacement endoprosthesis according to claim 1, wherein said joint replacement endoprosthesis is an endoprosthesis for a human knee joint.

3. The tibia plateau for a joint replacement endoprosthesis according to claim 1, wherein said curved contact line is an arcuate line.

4. The tibia plateau for a joint replacement endoprosthesis according to claim 1, wherein the bulge is discontinuous and is formed only at discrete points around the functional articulation surfaces.

5. The tibia plateau for a joint replacement endoprosthesis according to claim 1, wherein the bulge has a uniform slope in all directions as viewed from the functional articulation surfaces.

6. The tibia plateau for a joint replacement endoprosthesis according to claim 1, wherein the bulge has different slopes in different directions as viewed from the functional articulation surfaces.

7. The tibia plateau for a joint replacement endoprosthesis according to claim 1, wherein the bulge has a uniform height in all directions as viewed from the functional articulation surfaces.

8. The tibia plateau for a joint replacement endoprosthesis according to claim 1, wherein the bulge has different heights in different directions as viewed from the functional articulation surfaces.

9. The A tibia plateau for a joint replacement endoprosthesis comprising head and socket artificial joint parts having respective convex and concave functional articulation surfaces formed thereon, said artificial joint parts being arranged in pairs consisting of the head and the socket in contact with each other such that the functional articulation surfaces of the head and the socket are capable of rolling against one another along a curved contact line formed on the functional articulation surfaces, wherein a sloping bulge is formed adjacent the functional surfaces, which bulge limits the rolling movement and lateral displacement of the artificial joint parts, wherein the bulge has a linear slope.

10. The tibia plateau for a joint replacement endoprostheis according to claim 1, wherein the bulge has a slope with a concave curvature.

* * * * *